United States Patent
Fossen et al.

(10) Patent No.: US 10,370,581 B2
(45) Date of Patent: Aug. 6, 2019

(54) GAS HYDRATE INHIBITOR, METHOD AND USE OF HYPERBRANCHED POLYESTER POLYOLS AS GAS HYDRATE INHIBITORS

(71) Applicant: SINVENT AS, Trondheim (NO)

(72) Inventors: Martin Fossen, Trondheim (NO); Helene Konstantia Vralstad, Tanem (NO)

(73) Assignee: SINVENT AS, Trondheim (NO)

( * ) Notice: Subject to any disclaimer, the term of this patent is extended or adjusted under 35 U.S.C. 154(b) by 691 days.

(21) Appl. No.: 14/438,276

(22) PCT Filed: Oct. 28, 2013

(86) PCT No.: PCT/NO2013/050183
§ 371 (c)(1),
(2) Date: Apr. 24, 2015

(87) PCT Pub. No.: WO2014/065675
PCT Pub. Date: May 1, 2014

(65) Prior Publication Data
US 2015/0252246 A1    Sep. 10, 2015

(30) Foreign Application Priority Data

Oct. 26, 2012  (NO) .................................. 20121255

(51) Int. Cl.
| | | |
|---|---|---|
| *C09K 8/52* | (2006.01) | |
| *C10L 3/10* | (2006.01) | |
| *C07C 69/67* | (2006.01) | |
| *C08G 63/91* | (2006.01) | |

(52) U.S. Cl.
CPC .............. *C09K 8/52* (2013.01); *C07C 69/67* (2013.01); *C08G 63/91* (2013.01); *C10L 3/107* (2013.01); *C09K 2208/22* (2013.01)

(58) Field of Classification Search
CPC ...... C09K 8/52; C09K 2208/22; C07C 69/67; C10L 3/107; E21B 37/06; C08G 63/02; C08G 63/91
See application file for complete search history.

(56) References Cited

U.S. PATENT DOCUMENTS

| | | | | |
|---|---|---|---|---|
| 5,418,301 A | * | 5/1995 | Hult | C08G 63/12 525/437 |
| 2003/0057158 A1 | * | 3/2003 | Klomp | C10L 3/00 210/698 |
| 2008/0214865 A1 | | 9/2008 | Leinweber et al. | |
| 2009/0281271 A1 | * | 11/2009 | Bruchmann | C08G 63/20 528/302 |
| 2010/0144559 A1 | * | 6/2010 | Rivers | C09K 8/52 507/102 |
| 2014/0256599 A1 | * | 9/2014 | Kelland | C09K 8/52 507/90 |
| 2015/0184061 A1 | * | 7/2015 | Saboowala | C09K 8/52 166/305.1 |

FOREIGN PATENT DOCUMENTS

| | | |
|---|---|---|
| WO | 00/77070 | 12/2000 |
| WO | 01/77270 | 10/2001 |
| WO | 2008/017018 | 2/2008 |
| WO | 2011/075242 | 6/2011 |

OTHER PUBLICATIONS

Polymer Factory, http://www.polymerfactory.com/hyperbranched-polymers/polyester-amide/, accessed Jul. 27, 2017.*
Jena et al., "Hyperbranched Polyesters: Synthesis, Characterization, and Molecular Simulations", J. Phys. Chem. B 2007, 111, 8801-8811. (Year: 2007).*
International Search Report dated Jan. 16, 2014 in International (PCT) Application No. PCT/NO2013/050183.
Norwegian Search Report dated May 23, 2013 in Norwegian Priority Application No. 20121255.

* cited by examiner

*Primary Examiner* — In Suk C Bullock
*Assistant Examiner* — Ali Z Fadhel
(74) *Attorney, Agent, or Firm* — Wenderoth, Lind & Ponack, L.L.P.

(57) ABSTRACT

The present invention relates to a non-toxic and biodegradable low dosage gas hydrate inhibitor comprising hyperbranched polyester polyols having hydroxyl end groups which are chemically modified. Further, the invention relates to a method for controlling gas hydrate formation and plugging of gas hydrate forming fluids and the use of the gas hydrate inhibitors for this purpose.

12 Claims, No Drawings

GAS HYDRATE INHIBITOR, METHOD AND USE OF HYPERBRANCHED POLYESTER POLYOLS AS GAS HYDRATE INHIBITORS

TECHNICAL FIELD

The present invention relates to a new class of non-toxic and biodegradable low dosage hydrate inhibitors which will work as either an anti-agglomerant or a kinetic inhibitor or a combination. The invention also relates to a method for controlling gas hydrate formation and prevents plugging of gas hydrate forming fluids and the use of these hydrate inhibitors.

BACKGROUND/PRIOR ART

Gas hydrates are clathrate-type structures consisting of hydrogen-bonded water molecules that form "cages" that are stabilized by captured gas molecules like methane, propane, $CO_2$. Gas hydrates are normally formed under conditions of low temperatures and high pressures. During production of oil and gas, water is often co-produced resulting in a multi-phase system containing oil, water and gas. In addition also solid organic and inorganic particles may be present.

A large and increasing part oil and gas fields are situated subsea at large depths (high pressure) and low temperatures like in the Arctic where the formation of hydrates is very likely to occur, unless prevented by some artificial means. The formation of gas hydrates may lead to increased viscosity and potentially plugging of the well or process facilities including pipelines and valves. Hydrate plugs are a potential hazard which can lead to destruction of equipment and loss of life. In addition, remediation is both time consuming and expensive. Techniques for preventing the formation of gas hydrates or having a controlled hydrate formation are many. They include heating and/or insulation of the pipeline, production outside the hydrate region of the phase diagram, and finally the use of chemical inhibitors. Chemical inhibitors are used to remove hydrates, prevent hydrates from forming, or prevent hydrate particles to agglomerate and plug process equipment.

Often a combination of heating/insulation, depressurization etc. with chemical gas hydrate inhibitors are used. Hydrate inhibitors are divided into two main groups, Thermodynamic inhibitors and Low dosage inhibitors. The Thermodynamic hydrate inhibitors, THIs, are chemicals which shift the thermodynamic equilibrium of hydrates towards lower temperatures. They are added at very high concentrations, 10 to 60% relative to water, and facilities for their regeneration and recycling is therefore often required. The most common thermodynamic inhibitors used today are methanol and monoethylene glycol. Diethylene glycol is also used, but is less powerful. Triethylene glycol and ethanol are mainly used for removing smaller amounts of water from flow lines and process facilities so that hydrates cannot form.

The Low dosage inhibitors (injection rates less than 5%) are divided into kinetic inhibitors (KHI) and anti-agglomerates (AA). The KHIs are a class of molecules which delays the formation of gas hydrates for a period of time which is dependent on different process parameters like the subcooling, pressure and fluid composition. The polymers which constitute kinetic hydrate inhibitors do most often contain amide groups which make them polar, and a hydrocarbon chain which is adjacent to or directly bonded to the amide.

AAs do not prevent the formation of hydrate particles but stop them from agglomerating. Instead of plugging the hydrate particles are stabilized in and transported dispersed in the oil phase. Gas hydrate prevention by AAs therefore requires a continuous oil phase. AAs are surfactants of various molecular weights, like quaternary ammonium salts. Quaternary ammonium salts are generally very toxic and only partially biodegradable.

Effective hydrate inhibitors which are non-toxic and biodegradable, so called green" alternatives, are at present not commercially available. A few examples of biomolecules, like anti-freeze proteins and bio surfactants, which may function as gas hydrate inhibitors have been described in the literature.

This present invention relates to a new type of LDHIs which are both non-toxic and biodegradable. The molecular structure is of the type hyperbranched polyester polyol. Hyperbranched polymers are a class of polymers which extend radially in space with one potential branch point per repeating unit instead of forming long chains, like traditional linear polymers. The high degree of branching renders the structure compact and gives rise to a multitude of functional end groups which are available to chemical modification. Hyperbranched polymers have previously been used as gas hydrate inhibitors and some examples are given below.

One class of commercial KHIs is the hyperbranched poly(ester amide)s; cf. Villano et al, described in Chemical engineering Science 64 (2009) 3197-3200. The patent, WO/01/77270 describes adding to the mixture an amount of a dendrimeric compound effective to inhibit formation of hydrates at conduit temperatures and pressures, and flowing the mixture containing the dendrimeric compound and any hydrates through the conduit. Preferably, a hyperbranched polyester amide is used as hydrate formation inhibitor compound.

WO/2008/017007 discloses use of low dose gas hydrate inhibitors for controlling the gas hydrate formation in a well completion fluid in the annular space of hydrocarbon producing well. The low dosage gas hydrate inhibitors listed include low dosage hydrate inhibitors (LDHIs), kinetic hydrate inhibitors, dendrimeric or branched compound, linear polymers and copolymers and onium compounds. A particularly useful group of hydrate inhibitors include dendrimeric compounds and in particular hyperbranched polyester amides are mentioned. The highly branched dendrimeric compounds may have a number average molecular weight in the range of from about 100 to about 5000, with a molecular weight distribution of as broad as 2 to about 30.

US2006/0106265 describes a method for inhibiting formation of hydrocarbon gas hydrates. In this method a composition including at least one dendrimeric compound having a number average molecular weight of at least 1000 atomic mass unit is added. Preferably the dendrimeric compound is a branched or cross linked polymer. Hyperbranched polyester amides are mentioned as suitable compounds.

WO01/77270 relates to a method for inhibiting the plugging of a conduit, by inhibiting formation of hydrates. A dendrimeric compound effective to inhibit formation of hydrates is used. Preferably a hyperbranched polyesteramid where the condensation polymer contains ester groups and at least one amid group in the backbone and has a number average molecular between 500 and 50000 is used. The functional end groups (hydroxyl groups) of the polycondensation product can be modified by further reactions. Suitable modification can take place by reaction of at least part of the hydroxyl end groups with fatty acids.

US 2010/0018712 describes apparatus and methods for inhibiting formation of hydrocarbon hydrates and/or agglomerates. The low dosage hydrate inhibitors may be a kinetic inhibitor selected from the group consisting of dendrimeric compounds, hyperbranched polymers, linear polymers and copolymers.

US 2006/0218852 describes compositions useful for controlling formation of hydrates in various fluid systems. The composition comprises polymeric materials that are dendritic in nature or hyper-branched polyamino polymers.

Many of the hydrate inhibitors described in the prior art are based on polymers that are not environmentally friendly meaning either being toxic or non-degradable or both.

U.S. Pat. No. 5,418,301 relates to a dendritic macromolecule of the polyester type comprising a central initiator molecule or initiator polymer having one or more reactive hydroxyl groups. The dendritic macromolecule is intended for use as a component in applications such as alkyds, alkyd emulsions, saturated polyesters, unsaturated polyesters, epoxy resins, phenolic resins, polyurethane resins, polyurethane foams and elastomers, binders for radiation curing systems such as systems cured with ultra-violet (UV) and infra-red (IR) light or electron-beam (EB), dental materials, adhesives, synthetic lubricants, microlithographic paints, binders for powder systems, amino resins, composites reinforced with glass, aramid or carbon/graphite fibres and moulding compounds based on urea-formaldehyde resins, melamineformaldehyde resins or phenol-formaldehyde resins.

The inventors of the present invention have found that by modifying biodegradable and non-toxic hyperbranched polyester polyols by replacing one or more of the hydroxyl groups to obtain an amphiphilic structure, these modified polymers are useful for use as gas hydrate inhibitors.

SHORT SUMMARY OF THE INVENTION

The present invention provides a new family of non-toxic and biodegradable compounds based on hyperbranched polyester polyols and the use of such hyperbranched polyester polyols as gas hydrate inhibitors. The hyperbranched polyester is substituted at the terminal hydroxyl groups by hydrophobic or hydrophilic substituents to provide a suitable interaction of the polyester with the hydrate surface, hydrate cages by inclusion of the terminal groups, and the oil- and water phases. Examples of such hydrophobic substituents are aliphatic or aromatic substituents with a chain length between $C_1$ and $C_{40}$. Examples of such substituents are pentyl-, butyl-groups and various isomers thereof. The hyperbranched polyester may have either hydrophilic, hydrophobic or combination of hydrophilic and hydrophobic substituents. Examples of such hydrophilic substituents are acid functional groups.

In one aspect the present invention provides a gas hydrate inhibitor, comprising hyperbranched polyester polyols having hydroxyl end groups which are chemically modified.

In another aspect, the present invention provides a method for controlling gas hydrate formation and plugging of gas hydrate forming fluids, wherein a gas hydrate inhibitor according to claims 1-8 is added in crude oil, condensate and gas systems containing water.

The present invention is also directed to the use of composition comprising functionalized hyperbranched polyester polyols for controlling gas hydrate formation and plugging of gas hydrates.

DETAILED DESCRIPTION OF THE INVENTION

Hyperbranched polyester polyols having hydroxyl end groups which are chemically modified are suitable for use as gas hydrate inhibitors. They are added to crude oil, condensate and gas systems containing water. The hyperbranched polyester polyols according to present invention can be used alone or in combination with synergists. The synergists may be at least one selected from the group consisting of n-butanol, chitosan, 2-butoxyethanol, propanol and polysuccinimide, diglycol methyl ether, methanol and glycols (for example ethylene and polyethylene glycol and propylene and polypropylene glycols), non-polymeric surfactants with caprolactam or alkylamide head groups. Further, the modified hyperbranched polyester polyols can be mixed with at least one solvent selected from water, alcohols (examples are methanol, ethanol, propanol, butanol), aliphatic solvents (examples are hexane, and cyclohexane) aromatic solvents (examples are toluene, styrene, ethylbenzene), mineral oils (examples normal paraffins, isoparaffins and cycloparaffins, naphtenes, aromatics), esters (examples are butyl acetate, ethyl acetate, ketones (examples are acetone and 2-butanone) and ethers (examples are tetrahydrofuran, diglycol methyl ether, 1,4-dioxane, diethylether) before being used as gas hydrate inhibitors.

One example of a hyperbranched polyester polyol, poly-(2,2)-bismethylolpropanoic acid, described in U.S. Pat. No. 5,418,301, is readily degradable and degrades into non-toxic low molecular compounds. This polymer has a multitude of hydroxyl end groups and is prone to hydrogen bonding. The end groups can be modified to various extents with groups that render them amphiphilic, interact well with the hydrate surface etc.

Hyperbranched polymers can be produced by polymerization of monomers with the general formula $A_xB$ where A and B can react with each other and x is >1. For a product to be non-toxic and degradable both the product and the degradability products must also be non-toxic and/or degradable. Thus, the monomer used for making the hyperbranched polyester polyols in this invention should preferably be non-toxic and biodegradable. In this invention, A and B are hydroxyl- and carboxylic acid functional groups which can be reacted with each other to form covalent ester bonds. Other functional groups which can form ester bonds by reaction with alcohols are various carboxylic compounds such as acid chlorides and carboxylic anhydrides. The carboxylic acid can be selected from for example pivalic acid, dimethylbutyric acid, trimethylpentanoic acid, tert-butyl-trimethylpentanoic acid, diethylhexanoic acid or cyclopentanoic acid. An example of anhydride can be pivalic anhydride.

Below is schematically shown how a hyperbranched aliphatic polyester is formed from the monomer 2,2-bis methylolpropanoic acid.

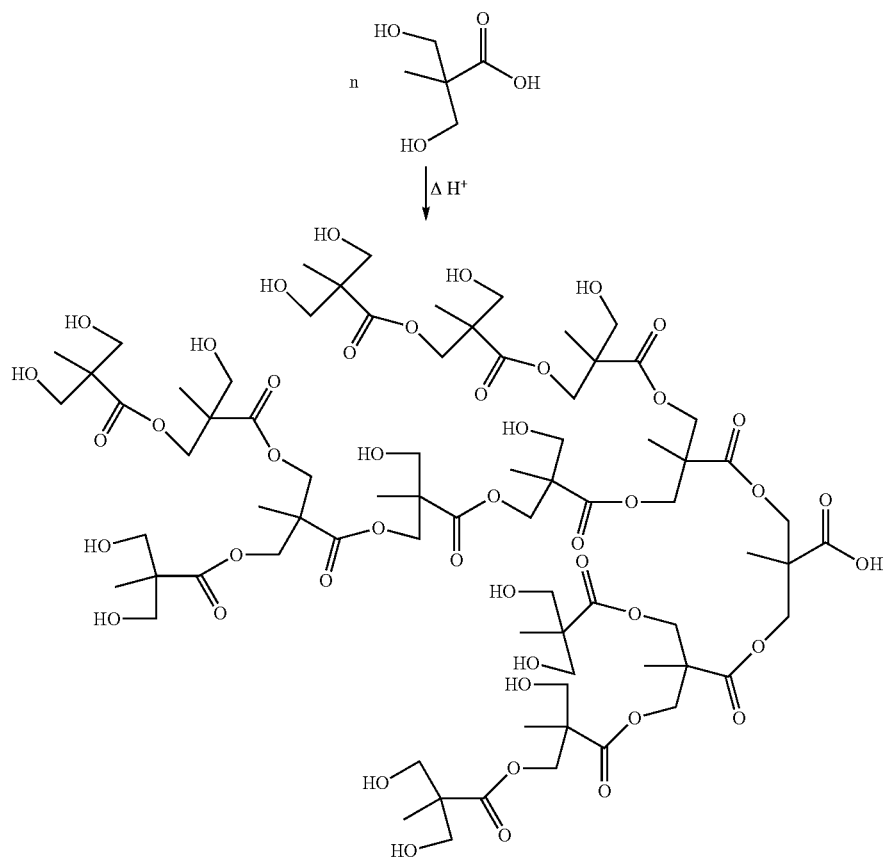

A suitable polymer for the production of the candidate hydrate inhibitors is the hyperbranched aliphatic polyester from the monomer 2,2-bis methylolpropanoic acid. This structure (of the monomer) is commercially available under the trade name Boltorn H20 from Perstorp AB. This polymer is degradable and forms non-toxic degradation products. The resulting polyester has an average molecular weight of 2100 g/mol and on an average 16 terminal hydroxyl groups available for chemical modification. The monomer and polymer will react with anhydrides and acids.

The monomer is soluble in polar solvents. Examples given, but not restricted to, are tetrahydrofuran (THF), acetone and methanol. The solubility of the polymer will depend on the degree of substitution of the hydroxyl groups with tert-butyl groups or other hydrophilic or hydrophobic groups. The functional groups substituting the hydroxyl end groups should be of a size and type fitting inside the cages of hydrates or interact with hydrates to lower subcooling and or prevent agglomeration of hydrate particles. One end group which will work well is a tert-butyl group however other groups are also relevant. Synergists can improve solubility of the monomer and polymers. Examples are n-butanol, chitosan, 2-butoxyethanol, propanol and polysuccinimide, methanol and glycols (for example ethylene and polyethylene glycol and propylene and polypropylene glycols), non-polymeric surfactants with caprolactam or alkylamide head groups.

Description of the Synthesis

Hyperbranched aliphatic polyester-based hydrate inhibitors can be produced by polymerization of the monomer 2,2-bismethylolpropionic acid and subsequently functionalization of the polymer by an aliphatic substituent to provide a suitable interaction with the hydrate, the aqueous phase and the oil phase. The degree of polymerization and molecular weight of the product can be controlled by controlling the experimental conditions of the polymerization. Similarly, those hydrate inhibitors can be produced by substitution of commercial hyperbranched polyols based on this monomer. To make the hyperbranched polymer amphiphilic and to provide suitable interaction with the cavities of the hydrates as well as the oil- and aqueous phases, the hydroxyl groups can be esterified with pivalic acid which gives terminal tert-butyl groups. Tert-butyl groups are known to have a size which fits well into the cavities of the gas hydrates. An alternative route to produce pivaloyl-substituted, hyperbranched polyesters is to react the terminal hydroxyl groups with pivalic anhydride.

In addition to tert-butyl groups other substituents may be used which have different hydrate inhibiting mechanisms. Polar terminal groups will form hydrogen bonds with water molecules thus having functionality closer to KHIs. Examples would be nitrogen, oxygen and sulphur containing species which also must be biodegradable and have a low toxicity. Examples of other non-polar substituents would be alkanes and cycloalkane substituents with carbon number from 1 to 8.

Description of Gas Hydrate Inhibiting Test

Comparisons of effects of different gas hydrate inhibitors in a mixture containing condensate, natural gas mixture and water with 3.5% by weight NaCl were performed.

A so called multicell apparatus, having 48 independent cells was used. The total volume of liquid filled to each cell was 3.4 mL and of this 30 percent by volume was water. Furthermore, 3 percent by weight, relative to the amount water, of the inhibitors was added. The inhibitors were dissolved in the water phase with or without help of methanol. A gas phase consisting of methane (70-95% by mole), ethane (0-5% by mole), propane (0-15% by mole), n-butane (0-5% by mole), nitrogen (0-5% by mole) and $CO_2$ (0-15% by mole) was used to pressurize the system to 70 bar. The system was cooled down to 4° C. under stirring and the movement of the stirrer was monitored and logged, as well as the temperature inside the cell. Formation of hydrates was detected by temperature increase in the individual cells. Effect of inhibitor was observed by delayed hydrate formation (subcooling) and/or continued stirring without plugging at temperatures lower than uninhibited systems. Total inhibition was defined as when the stirrer moved continuously throughout the temperature range both during cooling and re-heating. Distilled uninhibited brine had a hydrate formation temperature of 14.5° C. Some systems inhibited hydrate formation throughout the duration of the experiment while other systems lowered the subcooling within a temperature range of 4° C. to 13.5° C.

Substitution of Hyperbranched Polyesters

Examples describing the experimental procedure of reacting the terminal hydroxyl groups with pivalic anhydride and obtaining a product suitable for use as gas hydrate inhibitor.

Example 1

1.0 g hyperbranched polyester (Boltorn H20) was grinded and dispersed in 10 g THF. 0.10 g 4-(dimethylamino) pyridine (DMAP) was dissolved in the mixture. 0.5 g pivalic anhydride was added drop wise and the mixture was left under stirring at room temperature over night. After 20 hours the solvent was evaporated from the mixture, a clear solution, and the crude product was obtained as a viscous liquid.

This product obtained a subcooling of up to 8° C. before hydrate formation occurred. Movement of stirrer was observed down to 10° C. in condensate/brine/gas system.

Example 2

5.0 g hyperbranched polyester (Boltorn H20) was grinded and dispersed in 25 g THF. 0.50 g 4-(dimethylamino) pyridine (DMAP) was dissolved in the mixture. 3.5 g Pivalic anhydride was added drop-wise and the mixture was left under stirring at room temperature over night. After 20 hours the solvent was evaporated from the mixture, a clear solution, and the crude product was obtained as a viscous liquid.

This product obtained a subcooling of up to 9° C. before hydrate formation occurred. Movement of stirrer was observed down to and during 4° C.

Example 3

5.0 g hyperbranched polyester (Boltorn H20) was grinded and dispersed in 25 g THF. 0.75 g 4-(dimethylamino) pyridine (DMAP) was dissolved in the mixture. 5 g pivalic anhydride was added drop wise and the mixture was left under stirring at room temperature over night. After 20 hours the solvent was evaporated from the mixture, a clear solution, and the crude product was obtained as a viscous liquid.

This product obtained a subcooling of up to 7° C. Movement of stirrer was observed down to and during 4° C.

Example 4

2.0 g hyperbranched polyester (Boltorn H20) was grinded and dissolved together with 1, 56 g pivalic acid and 0.04 g p-toluenesulfonic acid monohydrate in a small amount of methanol. The methanol was evaporated and a small amount of toluene added. The mixture was heated and left to react under toluene reflux while evaporated water was continuously collected. When the theoretical amount of water was removed, the toluene was evaporated and the crude product was obtained as a sticky, viscous liquid.

This product obtained a subcooling of up to 7° C. Movement of stirrer was observed down to and during 4° C.

The following examples 5-8 describe further gas hydrate inhibitors according to the invention. The examples show procedures which differ in concentration of substituent and/or reaction time to control degree of substitution. These products are presently being tested according to the procedure described above.

Example 5

20.0 g 2,2-bismethylolpropanoic acid was added to a two-necked reactor which was immersed into a pre-heated oil bath at 140° C. The monomer was stirred at 100 rpm and 0.04 g concentrated sulfuric acid was added as a catalyst. After half an hour the reactor was flushed with nitrogen at low rate. 11.4 g pivalic acid was dissolved in a small amount of toluene and added to the reaction mixture. The reaction was left to react for another 3 hours.

Example 6

20.0 g 2,2-bismethylolpropanoic acid was added to a two-necked reactor which was immersed into a pre-heated oil bath at 140° C. The monomer was stirred at 100 rpm and 0.04 g concentrated sulfuric acid was added as a catalyst. After half an hour the reactor was flushed with nitrogen at low rate. 13.0 g dimethyl butyric acid was added to the reaction mixture. The reaction was left to react for another 3 hours.

Example 7

18.0 g 2,2-bismethylolpropanoic acid and 2.0 g 2,2-bismethylolbutanoic acid was added to a two-necked reactor which was immersed into a pre-heated oil bath at 140° C. The monomers were stirred at 100 rpm and 0.04 g concentrated sulfuric acid was added as a catalyst. After half an hour the reactor was flushed with nitrogen at low rate. After an additional 2 hours 9.26 g pivalic acid was dissolved in a small amount of toluene and added to the reaction mixture. The reaction was left to react for another 3 hours.

CONCLUSION

The results from the gas hydrate inhibiting tests performed on the examples 1 to 4 above show that the gas hydrate inhibitors according to present invention lead to a subcooling which delays hydrate formation and also prevents hydrates from plugging the system.

The invention claimed is:
1. A method for controlling gas hydrate formation and plugging in gas hydrate forming fluids, said method comprising:
adding a gas hydrate inhibitor comprising hyperbranched polyester polyols to crude oil, condensate, and gas systems containing water;
wherein the hyperbranched polyester polyols do not contain polyesteramide polyols, and wherein the hyperbranched polyester polyols have hydroxyl end groups which are chemically modified with a hydrophilic group and/or a hydrophobic group.

2. The method for controlling gas hydrate formation according to claim 1, wherein the hyperbranched polyester polyols are non-toxic and biodegradable.

3. The method for controlling gas hydrate formation according to claim 1, wherein all or parts of the chemically modified hydroxyl end groups are esterified with at least one hydrophilic group for increased water solubility.

4. The method for controlling gas hydrate formation according to claim 1, wherein all or parts of the chemically modified hydroxyl end groups are esterified with at least one hydrophobic group for increased amphiphilicity and hydrate interaction and/or increased oil solubility.

5. The method for controlling gas hydrate formation according to claim 4, wherein the hydrophobic group is introduced by reaction of the hyperbranched polyester polyol with a carboxylicacid and/or a carboxylic anhydride.

6. The method for controlling gas hydrate formation according to claim 5, wherein the carboxylic acid is selected from the group consisting of pivalic acid, dimethylbutyric acid, trimethylpentanoic acid, tert-butyl-trimethylpentanoic acid, diethylhexanoic acid, and cyclopentanoic acid.

7. The method for controlling gas hydrate formation according to claim 5, wherein the carboxylic anhydride is pivalic anhydride.

8. The method for controlling gas hydrate formation according to claim 1, wherein the chemically modified hydroxyl groups are replaced with amphiphilic groups.

9. The method according to claim 1, wherein the gas hydrate inhibitor is added alone or in combination with synergists.

10. The method according to claim 9, wherein the synergist is selected from the group consisting of n-butanol, chitosan, 2-butoxyethanol, propanol, polysuccinimide, methanol, glycols, and non-polymeric surfactants with caprolactam or alkylamide head groups.

11. The method according to claim 9, wherein the gas hydrate inhibitor is dissolved in a solvent before being added to the crude oil, condensate, and gas systems containing water.

12. The method according to claim 11, wherein the solvent is selected from the group consisting of water, alcohols, aliphatic solvent, aromatic solvents, mineral oils, esters, and ethers.

* * * * *